(12) United States Patent
Khavrutskii et al.

(10) Patent No.: US 11,345,653 B2
(45) Date of Patent: May 31, 2022

(54) COMPOSITIONS AND METHODS FOR REACTIVATING CHOLINESTERASES

(71) Applicants: The Henry M. Jackson Foundation for the Advancement of Military Medicine, Inc., Bethesda, MD (US); The Government of the United States as Represented by the Secretary of the Army, Fort Detrick, MD (US)

(72) Inventors: Ilja Khavrutskii, Brunswick, MD (US); Sven Anders Wallqvist, Frederick, MD (US)

(73) Assignees: The Henry M. Jackson Foundation for the Advancement of Military Medicine Inc., Bethesda, MD (US); The Government of the United States as Represented by the Secretary of the Army, Fort Detrick, MD (US)

( * ) Notice: Subject to any disclaimer, the term of this patent is extended or adjusted under 35 U.S.C. 154(b) by 183 days.

(21) Appl. No.: 16/310,686

(22) PCT Filed: Jun. 16, 2017

(86) PCT No.: PCT/US2017/037865
§ 371 (c)(1),
(2) Date: Dec. 17, 2018

(87) PCT Pub. No.: WO2017/218886
PCT Pub. Date: Dec. 21, 2017

(65) Prior Publication Data
US 2019/0345097 A1    Nov. 14, 2019

Related U.S. Application Data

(60) Provisional application No. 62/351,384, filed on Jun. 17, 2016.

(51) Int. Cl.
*C07C 215/68* (2006.01)

(52) U.S. Cl.
CPC ................ *C07C 215/68* (2013.01)

(58) Field of Classification Search
CPC ..................................... C07C 215/68
See application file for complete search history.

(56) References Cited

U.S. PATENT DOCUMENTS 3,517,057 A * 6/1970 Sandor ............... C07D 263/34
562/446

OTHER PUBLICATIONS

International Search Report issued in corresponding International Patent Application No. PCT/US2017/037865 dated Jul. 27, 2017.
Written Opinion issued in corresponding International Patent Application No. PCT/US2017/037865 dated Jul. 27, 2017.
Cadieux et al., "Probing the activity of a non-oxime reactivator for acetylcholinesterase inhibited by organophosphorus nerve agents," Chemico-Biological Interactions, 259: 133-141 (2016).
Tanaka et al., "A facile synthesis of 4-hydroxy- and 4-aminoidoles through corresponding indolines," Bulletin of the Chemical Society of Japan, 62: 3742 3744 (1989).
Khavrutskii et al., "Beta-Aminoalcohols as Potential Reactivators of Aged Sarin-/Soman-Inhibited Acetylcholine-sterase," Chemistryselect: Medicinal Chemistry & Drug Discovery, 2: 1885-1890 (2017).

* cited by examiner

*Primary Examiner* — Shawquia Jackson
(74) *Attorney, Agent, or Firm* — Sheppard Mullin Richter & Hampton LLP

(57) ABSTRACT

The invention relates to compounds, compositions and methods for activating, reactivating, reversing or preventing the deactivation of cholinesterases, such as acetylcholinesterase and butyrylcholinesterase.

14 Claims, 1 Drawing Sheet

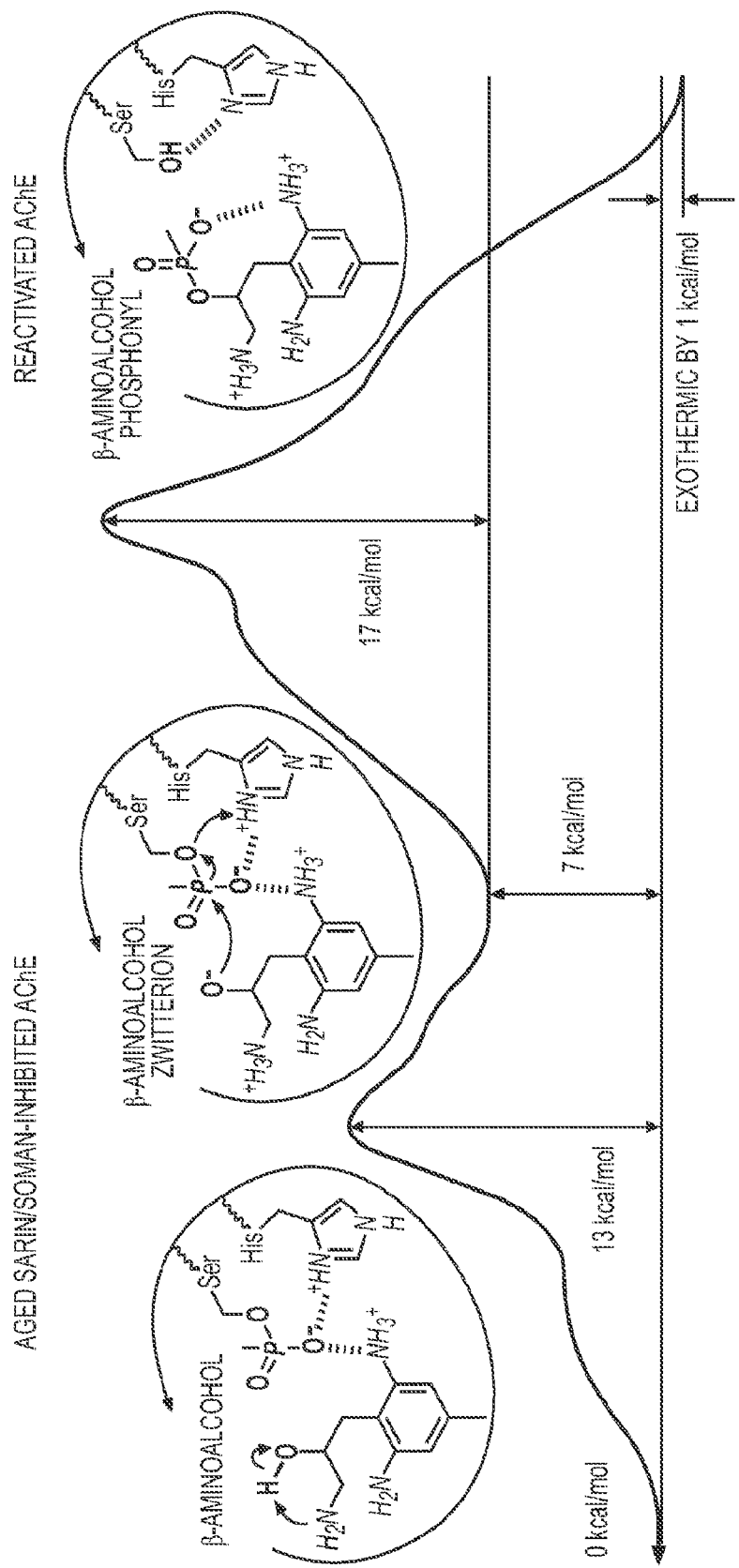

COMPOSITIONS AND METHODS FOR REACTIVATING CHOLINESTERASES

STATEMENT REGARDING FEDERALLY SPONSORED RESEARCH OR DEVELOPMENT

This invention was made with government support under Grant No. W81XWH-10-2-0029 awarded by The United States Army Medical Research and Materiel Command. The Government has certain rights in the invention.

BACKGROUND OF THE INVENTION

Field of the Invention

The invention relates to compounds, compositions and methods for activating, reactivating, reversing or preventing the deactivation of cholinesterases, such as acetylcholinesterase and butyrylcholinesterase.

SUMMARY OF THE INVENTION

The invention relates to compounds, compositions and methods for activating, reactivating, reversing or preventing the deactivation of a cholinesterase, with the compounds comprising a compound of Formula I:

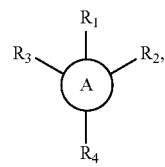

(I)

or a pharmaceutically acceptable salt or prodrug thereof, wherein

is a 5- or 6-membered substituted or unsubstituted aromatic ring, a 5- or 6-membered substituted or unsubstituted cycloalkyl, a 5- or 6-membered substituted or unsubstituted heteroaryl or a 5- or 6-membered substituted or unsubstituted heterocyclic ring, $R_1$ is $R_5C(R_6)(OH)R_7C(R_8)(NH_2)R_9$;

$R_2$ and $R_3$ are independently selected from the group consisting of H, CN, $OR_{10}$, $S(O)_{0-2}R_{10}$, $NR_{11}R_{12}$, $C(O)NR_{13}R_{14}$, $C_{1-6}$ alkyl, and $C_{1-6}$ alkene, wherein at least one of $R_2$ and $R_3$ is proximal to $R_1$, and at least one of $R_2$ and $R_3$ is $NR_{11}R_{12}$;

$R_4$ is selected from the group consisting of H, CN, $OR_{10}$, $S(O)_{0-2}R_{10}$, $C_{1-6}$ alkyl, $C_{1-6}$ alkene, $NR_{11}R_{12}$ and $C(O)NR_{13}R_{14}$;

$R_5$ is selected from the group consisting of a bond, $C_{1-4}$ alkyl and $C_{1-4}$ alkene;

$R_6$ is selected from the group consisting of H and $C_{1-3}$ alkyl;

$R_7$ is selected from the group consisting of a bond, substituted or unsubstituted $C_{1-3}$ alkyl and substituted or unsubstituted $C_{1-3}$ alkene;

$R_8$ is selected from the group consisting of $C(O)NHR_{15}$ and $C(O)OR_{15}$;

$R_9$ is selected from the group consisting of H, CN, $C(R_6)OH$, $OR_8$, $NR_9R_{10}$, $C(O)NR_{11}R_{12}$, $C_{1-6}$ alkyl and $C_{1-6}$ alkene;

$R_{10}$ is selected from the group consisting of H, $C_{1-3}$ alkyl and $C_{6-12}$ aryl;

$R_{11}$, $R_{12}$, $R_{13}$, and $R_{14}$ are independently selected from the group consisting of H, $C_{1-4}$ alkyl and $C_{1-4}$ alkene, and $R_{15}$ is selected from the group consisting of H and $C_{1-3}$ alkyl, wherein at least one of $R_{11}$ and $R_{12}$ is H.

BRIEF DESCRIPTION OF THE DRAWINGS

FIG. 1 depicts the positively charged $R_2$ or $R_3$ amino group of molecule 101, below, hydrogen bonded to a phosphonyl group in an inactivated acetylcholinesterase (AChE) enzyme. The hydrogen bonding allows the catalytic histidine residue in AChE to transfer its proton to the oxygen of the phosphonylated serine residue. The reactivation with molecule 101 was slightly exothermic by 1.1 kcal/mol. Furthermore, the optimized reaction paths revealed an intermediate. The intermediate corresponded to an intramolecular proton transfer within the nucleophilic β-aminoalcohol group of molecule 101 that created a zwitterionic β-amino-alcohol group with negatively charged oxygen for the nucleophilic attack and a positively charged β-$NH_3^+$ group. This intermediate was metastable and had energy of 7.2 kcal/mol. The barrier for the formation of this intermediate was 13.5 kcal/mol.

DETAILED DESCRIPTION OF THE INVENTION

The invention relates to compounds, compositions and methods for activating, reactivating, reversing or preventing the deactivation of a cholinesterase, such as acetylcholinesterase and/or butyrylcholinesterase. The methods comprise administering at least one compound in an amount sufficient to activate, reactivate, inhibit or reverse the deactivation of acetylcholinesterase, with the at least one compound being a compound of formula I:

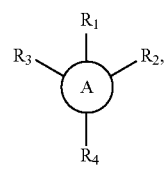

(I)

or a pharmaceutically acceptable salt or prodrug thereof, wherein

is a 5- or 6-membered substituted or unsubstituted aromatic ring, a 5- or 6-membered substituted or unsubstituted cycloalkyl, a 5- or 6-membered substituted or unsubstituted heteroaryl or a 5- or 6-membered substituted or unsubstituted heterocyclic ring, $R_1$ is $R_5C(R_6)(OH)R_7C(R_8)(NH_2)R_9$;

$R_2$ and $R_3$ are independently selected from the group consisting of H, CN, $OR_{10}$, $S(O)_{0-2}R_{10}$, $NR_{11}R_{12}$, $C(O)NR_{13}R_{14}$, $C_{1-6}$ alkyl, and $C_{1-6}$ alkene, wherein at least one of $R_2$ and $R_3$ is proximal to $R_1$, and at least one of $R_2$ and $R_3$ is $NR_{11}R_{12}$;

$R_4$ is selected from the group consisting of H, CN, $OR_{10}$, $S(O)_{0-2}R_{10}$, $C_{1-6}$ alkyl, $C_{1-6}$ alkene, $NR_{11}R_{12}$ and $C(O)NR_{13}R_{14}$;

$R_5$ is selected from the group consisting of a bond, $C_{1-4}$ alkyl and $C_{1-4}$ alkene;

$R_6$ is selected from the group consisting of H and $C_{1-3}$ alkyl;

$R_7$ is selected from the group consisting of a bond, substituted or unsubstituted $C_{1-3}$ alkyl and substituted or unsubstituted $C_{1-3}$ alkene;

$R_8$ is selected from the group consisting of $C(O)NHR_{15}$ and $C(O)OR_{15}$;

$R_9$ is selected from the group consisting of H, CN, $C(R_6)OH$, $OR_8$, $NR_9R_{10}$, $C(O)NR_{11}R_{12}$, $C_{1-6}$ alkyl and $C_{1-6}$ alkene;

$R_{10}$ is selected from the group consisting of H, $C_{1-3}$ alkyl and $C_{6-12}$ aryl;

$R_{11}$, $R_{12}$, $R_{13}$, and $R_{14}$ are independently selected from the group consisting of H, $C_{1-4}$ alkyl and $C_{1-4}$ alkene, and $R_{15}$ is selected from the group consisting of H and $C_{1-3}$ alkyl, wherein at least one of $R_{11}$ and $R_{12}$ is H.

In one embodiment, at least one of $R_2$ or $R_3$ should be ionizable. In one specific embodiment, at least one of $R_2$ or $R_3$ should be protonatable, i.e., a proton acceptor. In a more specific embodiment, the group $NR_{11}R_{12}$ is a proton acceptor.

As used herein and unless otherwise indicated, the term "alkyl" means a substituted or unsubstituted, saturated, linear or branched hydrocarbon chain radical. Examples of alkyl groups include, but are not limited to, $C_{1-15}$ linear, branched or cyclic alkyl, such as methyl, ethyl, propyl, isopropyl, cyclopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, sec-butyl, t-butyl, cyclobutyl, pentyl, isopentyl, neopentyl, hexyl, and cyclohexyl and longer alkyl groups, such as heptyl, octyl, nonyl and decyl. An alkyl can be unsubstituted or substituted with one or two suitable substituents.

As used herein and unless otherwise indicated, the terms "alkoxy" or "alkyloxy" means an —O— alkyl, wherein alkyl is as defined herein. An alkoxy can be unsubstituted or substituted with one or two suitable substituents. Preferably, the alkyl chain of an alkyloxy is from 1 to 5 carbon atoms in length, referred to herein, for example, as "$C_{1-5}$ alkoxy." In one embodiment, the alkyl chain of an alkyloxy is from 1 to 10 carbon atoms in length, referred to herein, for example, as "$C_{1-10}$ alkoxy."

As used herein and unless otherwise indicated, the terms "alkene" or "alkenyl group" means a monovalent linear, branched or cyclic hydrocarbon chain having one or more double bonds therein. The double bond of an alkene can be unconjugated or conjugated to another unsaturated group. An alkene can be unsubstituted or substituted with one or two suitable substituents. Suitable alkenes include, but are not limited to $C_{2-8}$ alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkene can be unsubstituted or substituted with one or two suitable substituents.

As used herein and unless otherwise indicated, the term "aryl" or "aromatic ring" means a monocyclic or polycyclic conjugated ring structure that is well known in the art. Examples of suitable aryl groups or aromatic rings include, but are not limited to, phenyl, tolyl, anthacenyl, fluorenyl, indenyl, azulenyl, and naphthyl. An aryl group can be unsubstituted or substituted with one or two suitable substituents. In one embodiment, the aryl group is a monocyclic ring, wherein the ring comprises 6 carbon atoms, referred to herein as "$C_6$ aryl."

"Substituted aryl" includes an aryl group optionally substituted with one or more functional groups, such as halo, alkyl, haloalkyl (e.g., trifluoromethyl), alkoxy, haloalkoxy (e.g., difluoromethoxy), alkenyl, alkynyl, aryl, heteroaryl, arylalkyl, aryloxy, aryloxyalkyl, arylalkoxy, alkoxycarbonyl, alkylcarbonyl, arylcarbonyl, arylalkenyl, aminocarbonylaryl, arylthio, arylsulfinyl, arylazo, heteroarylalkyl, heteroarylalkenyl, heteroaryloxy, hydroxy, nitro, cyano, amino, substituted amino wherein the amino includes 1 or 2 substituents (which are optionally substituted alkyl, aryl or any of the other substituents recited herein), thiol, alkylthio, arylthio, heteroarylthio, arylthioalkyl, alkoxyarylthio, alkylaminocarbonyl, arylaminocarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfonaminocarbonyl and/or any of the alkyl substituents recited herein.

The term "heteroaryl" as used herein alone or as part of another group refers to a 5- to 7-membered aromatic ring which includes 1, 2, 3 or 4 hetero atoms such as nitrogen, oxygen or sulfur and such rings fused to an aryl, cycloalkyl, heteroaryl or heterocycloalkyl ring (e.g. benzothiophenyl, indolyl), and includes possible N-oxides. "Substituted heteroaryl" includes a heteroaryl group optionally substituted with 1 to 4 substituents, such as the substituents included above in the definition of "substituted alkyl" and "substituted cycloalkyl." Substituted heteroaryl also includes fused heteroaryl groups which include, for example, quinoline, isoquinoline, indole, isoindole, carbazole, acridine, benzimidazole, benzofuran, isobenzofuran, benzothiophene, phenanthroline, purine, and the like.

Moreover, the terms "heterocyclo," "heterocycle," or "heterocyclic ring," as used herein, refer to an unsubstituted or substituted stable 5- to 7-membered monocyclic ring system which may be saturated or unsaturated, and which consists of carbon atoms and from one to four heteroatoms selected from N, O or S, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but are not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinylsulfoxide, thiamorpholinylsulfone, and oxadiazolyl.

As used herein, the term "optionally substituted" may indicate that a chemical moiety referred to, for example, alkyl, aryl, heteroaryl, may be unsubstituted or substituted with one or more groups including, without limitation, alkyl, alkenyl, alkynyl, cycloalkyl, arylalkyl, aryl, heterocycle, heteroaryl, hydroxyl, amino, alkoxy, halogen, carboxy, carbalkoxy, carboxamido, monoalkylaminosulfinyl, dialkylaminosulfinyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, dialkylaminosulfinylalkyl and the like. The chemical moieties of Formula I may be optionally substituted alkyl, alkenyl, alkynyl, cycloalkyl, arylalkyl, aryl, heterocycle or heteroaryl. For example, optionally substituted alkyl may include both propyl and 2-chloro-propyl. Additionally, "optionally substituted" is also inclusive of embodiments where the named substituent or substituents have multiple substituents rather than simply a single substituent. For example, optionally substituted aryl may include both phenyl and 3-methyl-5-ethyl-6-chloro-phenyl.

The term "cycloalkyl" includes saturated or partially unsaturated (containing 1 or more double bonds) cyclic hydrocarbon groups containing 1 to 3 rings, including monocyclicalkyl, bicyclicalkyl and tricyclicalkyl, containing a total of 3 to 20 carbons forming the rings, or about 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl, cyclododecyl, and cyclohexenyl.

"Substituted cycloalkyl" includes a cycloalkyl group optionally substituted with 1 or more substituents such as halogen, alkyl, substituted alkyl, alkoxy, hydroxy, aryl, substituted aryl, aryloxy, cycloalkyl, alkylamido, alkanoylamino, oxo, acyl, arylcarbonylamino, amino, nitro, cyano, thiol and/or alkylthio and/or any of the substituents included in the definition of "substituted alkyl."

As used herein and unless otherwise indicated, the term "aryloxy" means an —O-aryl group, wherein aryl is as defined herein. An aryloxy group can be unsubstituted or substituted with one or two suitable substituents. Preferably, the aryl ring of an aryloxy group is a monocyclic ring, wherein the ring comprises 6 carbon atoms, referred to herein as "$C_6$ aryloxy."

As used herein and unless otherwise indicated, the term "ether" means a group of formula alkyl-O-alkyl, alkyl-O-alkynyl, alkyl-O-aryl, alkenyl-O-alkenyl, alkenyl-O-alkynyl, alkenyl-O-aryl, alkynyl-O-alkynyl, alkynyl-O-aryl, aryl-O-aryl, wherein "alkyl", "alkenyl", "alkynyl" and "aryl" are defined herein.

As used herein and unless otherwise indicated, the term "carboxy" means a radical of the formula: —COOH.

As used herein and unless otherwise indicated, the term "halogen" means fluorine, chlorine, bromine, or iodine. Correspondingly, the meaning of the terms "halo" and "Hal" encompass fluoro, chloro, bromo, and iodo.

As used herein and unless otherwise indicated, the terms "substituted" and "suitable substituent" mean groups that do not nullify the synthetic or pharmaceutical utility of the compounds of the invention or the intermediates useful for preparing them. Examples of substituted groups or suitable substituents include, but are not limited to: $C_{1-10}$ alkyl; $C_{1-10}$ alkenyl; $C_{1-10}$ alkynyl; $C_6$ aryl; $C_{3-5}$ heteroaryl; $C_{3-7}$ cycloalkyl; $C_{1-10}$ alkoxy; $C_6$ aryloxy; —CN; —OH; SH; oxo; halo; —NO$_2$; —CO$_2$H; —NH$_2$; —NHOH; —NH($C_{1-10}$ alkyl); —N($C_{1-10}$ alkyl)$_2$; —NH($C_6$ aryl); —NHO($C_{1-10}$ alkyl); —N(O$C_{1-10}$ alkyl)$_2$; —NH(O$C_6$ aryl); —S($C_{1-10}$ alkyl); —S($C_6$ aryl); (=O); —N($C_6$ aryl)$_2$; —CHO; —C(O)($C_{1-10}$ alkyl); —C(O)($C_6$ aryl); —C(O)O($C_{1-10}$ alkyl); and —C(O)O($C_6$ aryl), —C(S)($C_{1-10}$ alkyl); —C(S)($C_6$ aryl); —SO$_2$ ($C_{1-10}$ alkyl); —SO$_2$($C_6$ aryl); —SO($C_{1-10}$ alkyl); —SO($C_6$ aryl), and —SO$_3$H, —C(S)O($C_{1-10}$ alkyl); —C(S)O$C_6$ aryl. In certain illustrative embodiments, the substituents can be one or more than one suitable groups, such as, but not limited to, —F, —Cl, —Br, —I, —OH, azido, —SH, alkyl, aryl, heteroalky, alkyoxyl, alkylthiol, amino, hydroxylamino, N-alkylamino, —N,N-dialkylamino, —N,N-dimethylamino, acyl, alkyloxycarbonyl, sulfonyl, urea, —NO2, and triazolyl. One of skill in art can readily choose a suitable substituent based on the stability and pharmacological and synthetic activity of the compound of the invention.

As used herein, the term "proximal," when used in conjunction with a chemical group, is relative term and is used to mean that one group is immediately adjacent to another group. For example, if each of the groups in question is on a 6-membered ring, the terms "proximal" would be synonymous with "ortho." With 5-membered rings, however, the naming convention of a 6-membered ring may not apply.

As used herein and unless otherwise indicated, the term "compounds of the invention" means, collectively, the compounds of Formula I and pharmaceutically acceptable salts thereof as well as specific compounds depicted herein. The compounds of the invention are identified herein by their chemical structure and/or chemical name. Where a compound is referred to by both a chemical structure and a chemical name, and that chemical structure and chemical name conflict, the chemical structure is determinative of the compound's identity. The compounds of the invention may contain one or more chiral centers and/or double bonds and, therefore, exist as stereoisomers, such as double-bond isomers (i.e., geometric isomers), enantiomers, or diastereomers. According to the invention, the chemical structures depicted herein, and therefore the compounds of the invention, encompass all of the corresponding compound's enantiomers and stereoisomers, that is, both the stereomerically pure form (e.g., geometrically pure, enantiomerically pure, or diastereomerically pure) and enantiomeric and stereoisomeric mixtures. Enantiomeric and stereoisomeric mixtures can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically- or enantiomerically-pure intermediates, reagents, and catalysts by well-known asymmetric synthetic methods.

The phrase "pharmaceutically acceptable salt(s)," as used herein includes but is not limited to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions including, but not limited to, sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium and iron salts.

Specific embodiments of the invention encompass but are not limited to:

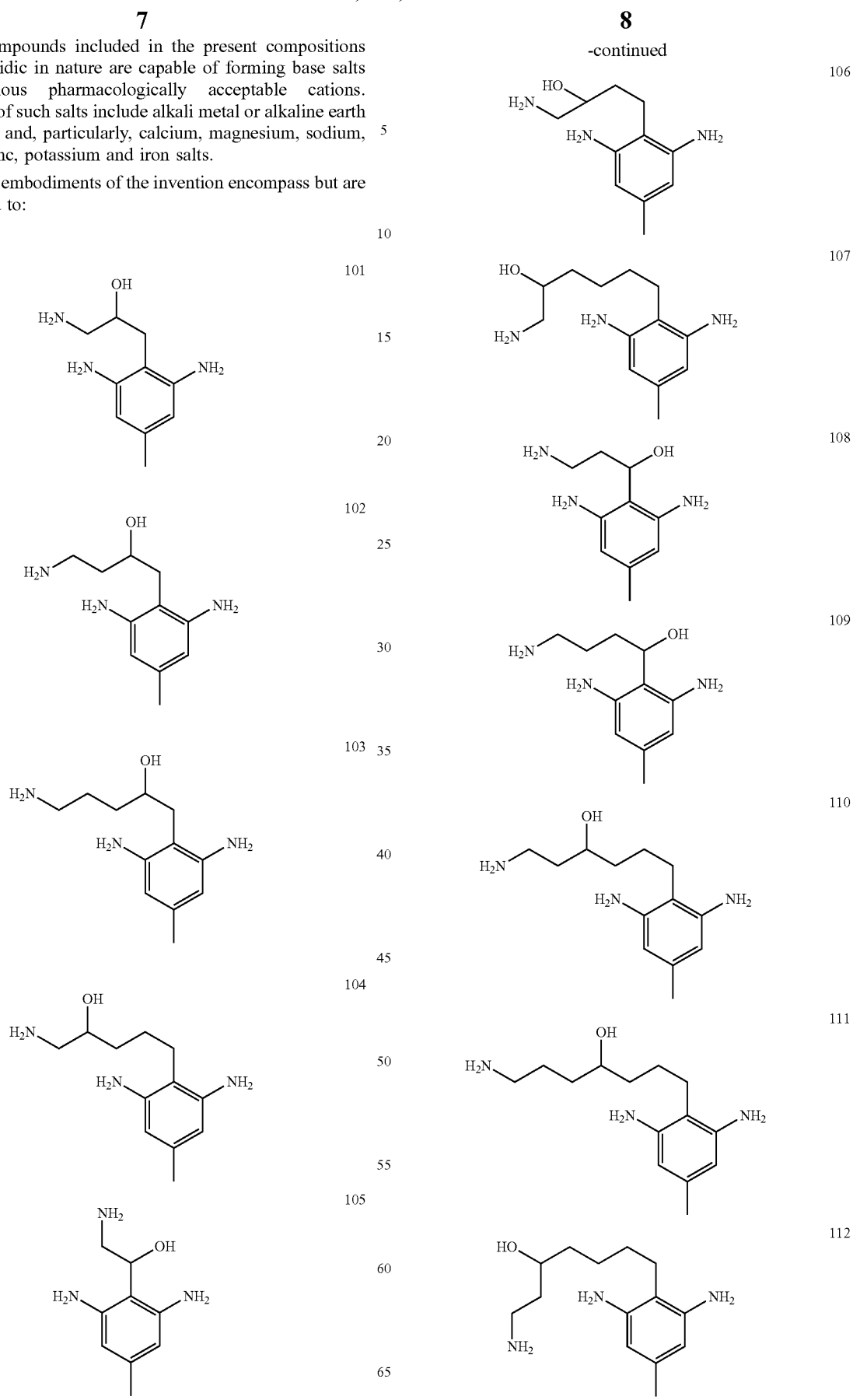

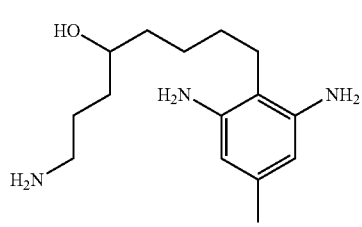
113
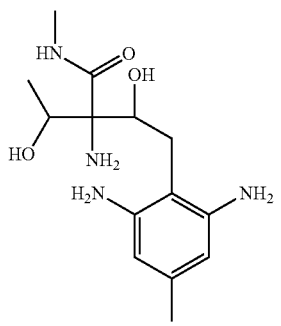
114
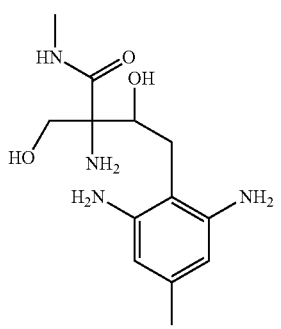
115
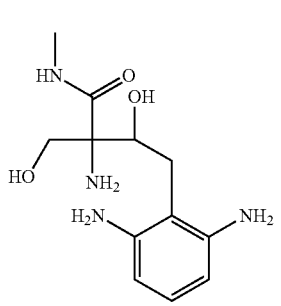
116
117
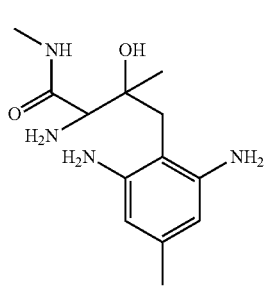
118
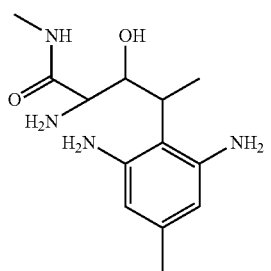
119
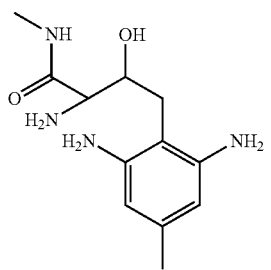
120
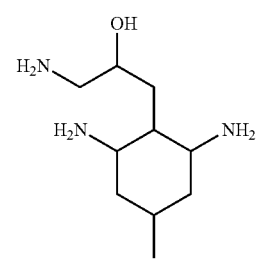
201
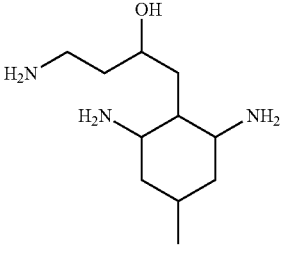
202
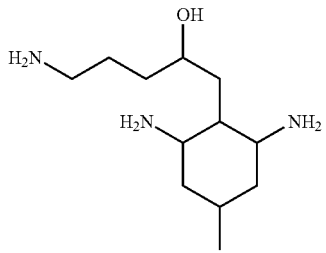
203

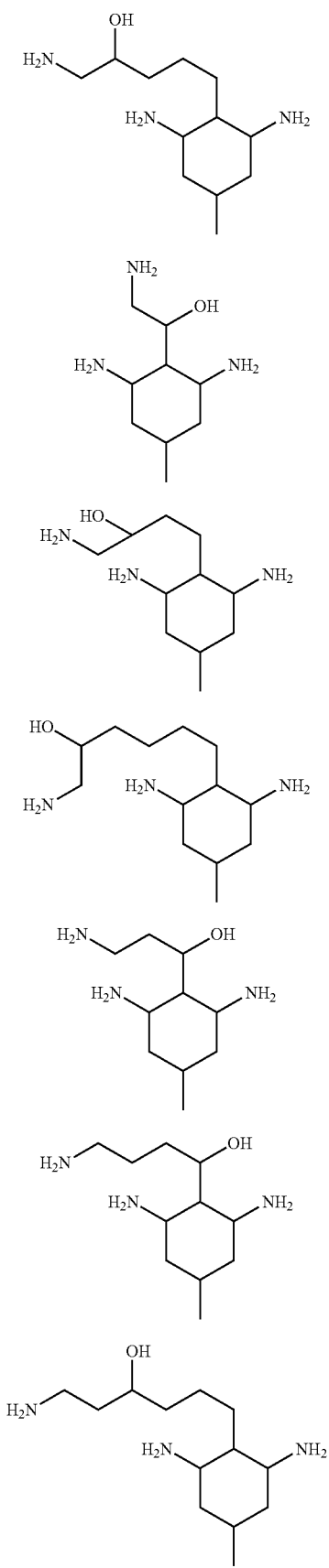
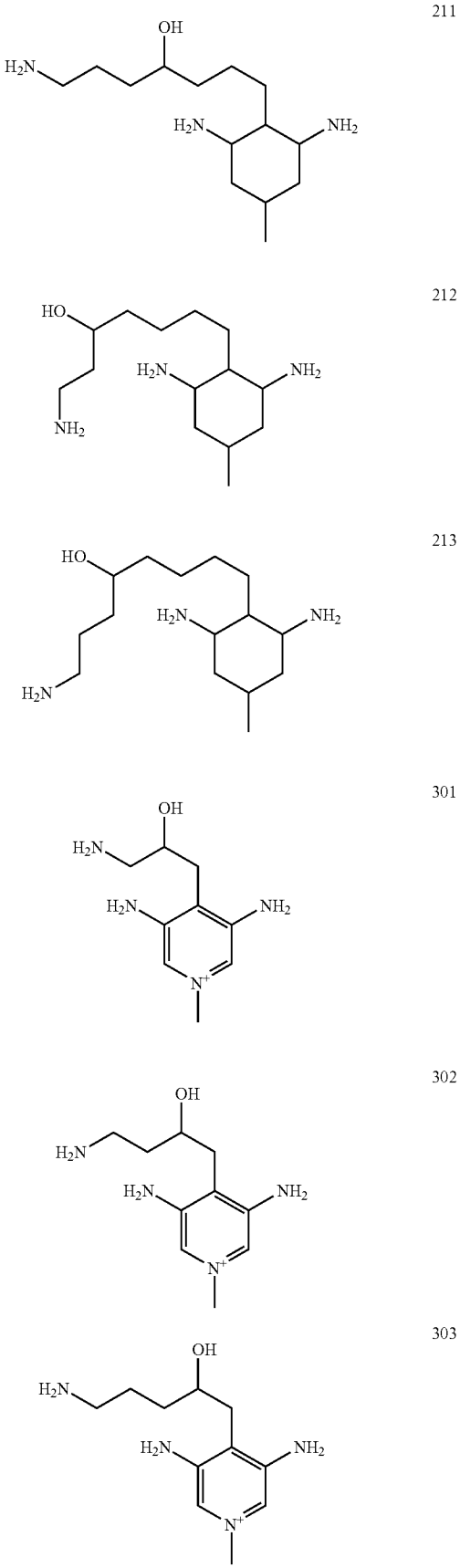

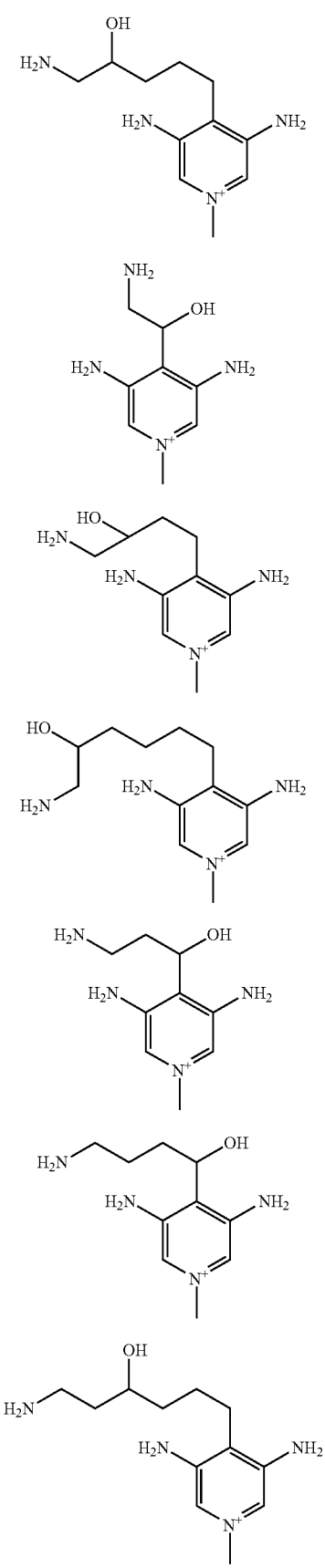

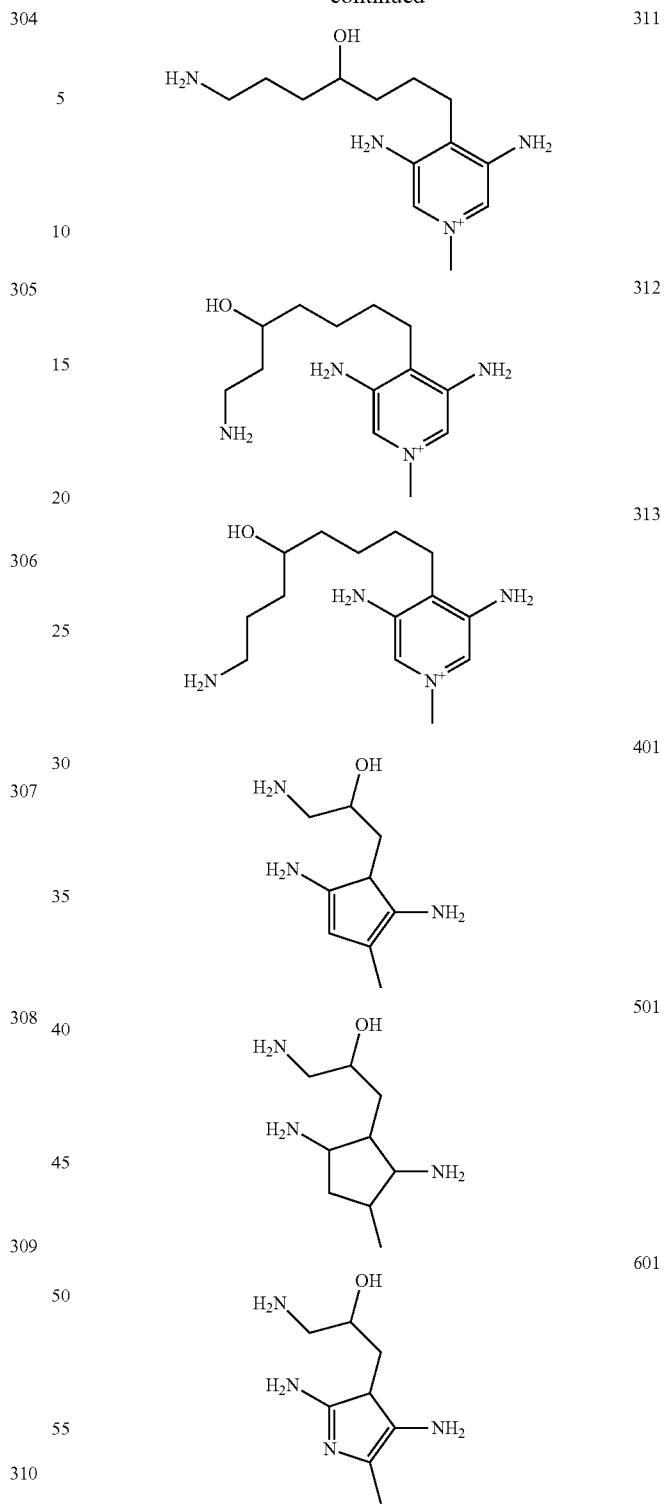

It will be understood that above compounds are illustrative only and not intended to limit the scope of the claims to only those compounds. The compounds of the invention can be synthesized by organic chemistry techniques known to those of ordinary skill in the art.

As used herein and unless otherwise indicated, the term "pharmaceutically acceptable prodrug" means a derivative of a compound that can hydrolyze, oxidize, or otherwise react under biological conditions, in vitro or in vivo, to provide the compound. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include but are not limited to compounds that comprise oligonucleotides, peptides, lipids, aliphatic and aromatic groups, or NO, $NO_2$, ONO, and $ONO_2$ moieties. Prodrugs can typically be prepared using well known methods, such as those described in Burger's Medicinal Chemistry and Drug Discovery, pp. 172, 178, 949, 982 (Manfred E. Wolff ed., 5th ed. 1995), and Design of Prodrugs (H. Bundgaard ed., Elsevier, N.Y. 1985).

As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, lower acyloxyalkyl esters (such as acetoxylmethyl, acetoxyethyl, aminocarbonyloxy-methyl, pivaloyloxymethyl, and pivaloyloxyethyl esters), lactonyl esters (such as phthalidyl and thiophthalidyl esters), lower alkoxyacyloxyalkyl esters (such as methoxycarbonyloxy-methyl, ethoxycarbonyloxyethyl and isopropoxycarbonyloxyethyl esters), alkoxyalkyl esters, choline esters, and acylamino alkyl esters (such as acetamidomethyl esters). Examples of biohydrolyzable amides include, but are not limited to, lower alkyl amides, amino acid amides, alkoxyacyl amides, and alkylaminoalkyl-carbonyl amides. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, the term "cholinesterase" is a general terms that refers to either acetylcholinesterase or butyrylcholinesterase. Typically, acetylcholinesterase (AChE) is found in chemical synapses and neuromuscular junctions in an "active" state. AChE catalyzes the breakdown of acetylcholine to acetate and choline to block the action of acetylcholine on its receptors. Certain compounds, however, such as but not limited to nerve toxins and pesticides can inactivate AChE. For example, organophosphorous compounds can form a covalent adduct with AChE thereby preventing AChE from functioning to block the action of acetylcholine. If left untreated, exposure to organophosphates can result in neurological damage, loss of muscle function and even death.

Organophosphates affect the activity of AChE in a two-stage process. First, the organophosphate compounds can form a covalent adduct with the enzyme, thereby immediately inhibiting the function of AChE. Once deactivated, the AChE enzyme then undergoes a dealkylation reaction known as "aging." This dealkylatyion reaction is considered irreversible, thereby rendering the aged AChE as non-functional. As used herein, the term "non-aged, inactive AChE" is used to mean AChE that has formed a covalent adduct, and is thus inactive, but has not yet irreversibly aged. The compounds of the present invention are useful in reactivating non-aged, inactive AChE as well as aged (or dealkylated) AChE. Moreover, the compounds of the present invention are also useful in preventing dealkylation of AChE. Accordingly, "reactivation of acetylcholinesterase" is used herein to mean the reactivation of non-aged, inactive AChE as well as conversion of aged (or dealkylated) AChE into an active state. The term "reactivation of acetylcholinesterase," however, does not mean or imply that the compounds of the present invention will necessarily re-alkylate aged AChE. The term "preventing the aging of acetylcholinesterase" or "interfering with the aging of acetylcholine esterase" are used herein to mean that the compounds of the present invention can be used to prevent or interfere with the dealkylation of AChE that has been or could be exposed to an inactivating compound, such as but not limited to an organophosphate, thereby preventing the "aging" or permanent inactivation of AChE. The terms "preventing the aging of acetylcholinesterase" or "interfering with the aging of acetylcholine esterase" can also be used to mean the reactivation of non-aged, inactive AChE. Examples of inactivating agents include but are not limited to sarin, cyclosarin, tabun, soman and V-agents such as but not limited to VX and VR and organophosphate pesticides such as paraoxon. It is not necessary, however, that AChE would have been previously exposed to an inactivating compound to perform methods of preventing or interfering with the deactivation of AChE.

The enzyme butyrylcholinesterase (BChE) is produced in the liver and is generally found in the circulation. Similar to AChE, BChE also hydrolyzes acetylcholine as well as many other esters. BChE is believed to act on certain drugs and toxins in the circulation prior to these substances reaching the central nervous system. For example, genetic mutations in subjects leading to deficiencies of active BChE often results in increased sensitivity to choline ester drugs and other drugs and toxins. Similar to AChE, organophosphorous compounds can also inactivate BChE by a similar two-stage process as when organophosphates deactivate AChE. The BChE enzyme forms a covalent adduct with the organophosphates and subsequently undergoes a dealkylation reaction to "age" the BChE enzyme.

The methods of the present invention relate to administering to a subject a composition comprising a compound of Formula I or at least one of the specific compounds depicted herein. Specifically, the methods include methods of reactivating AChE or preventing the deactivation of AChE in a subject in need thereof comprising administering to the subject a compound of Formula I or at least one of the specific compounds depicted herein. For example, the methods of the present invention include treating a subject for toxicity associated with AChE inactivation, with the methods comprising administering a therapeutically effective amount of at least one compound of Formula I or at least one of the specific compounds depicted herein.

In specific embodiments, the methods of the present invention relate to administering to a subject a composition comprising a therapeutically effective amount of at least one compound of 101, 102, 103, 104, 105, 106, 107, 108, 109, 110, 111, 112, 113, 114, 115, 116, 117, 118, 119, 120, 201, 202, 203, 204, 205, 206, 207, 208, 209, 210, 211, 212, 213, 301, 302, 303, 304, 305, 306, 307, 308, 309, 310, 311, 312, 313, 401, 501 or 601 to treat or prevent toxicity associated with AChE inactivation to a subject in need of treatment thereof.

The methods of the present invention relate to administering to a subject a composition comprising a compound of Formula I or at least one of the specific compounds depicted herein. Specifically, the methods include methods of reactivating BChE or preventing the deactivation of BChE in a subject in need thereof comprising administering to the subject a compound of Formula I or at least one of the specific compounds depicted herein. For example, the methods of the present invention include treating a subject for toxicity associated with BChE inactivation, with the methods comprising administering a therapeutically effective amount of at least one compound of Formula I or at least one of the specific compounds depicted herein.

In specific embodiments, the methods of the present invention relate to administering to a subject a composition comprising a therapeutically effective amount of at least one compound of 101, 102, 103, 104, 105, 106, 107, 108, 109, 110, 111, 112, 113, 114, 115, 116, 117, 118, 119, 120, 201, 202, 203, 204, 205, 206, 207, 208, 209, 210, 211, 212, 213, 301, 302, 303, 304, 305, 306, 307, 308, 309, 310, 311, 312, 313, 401, 501 or 601 to treat or prevent toxicity associated with BChE inactivation to a subject in need of treatment thereof.

As used herein, the term "administer" or "administering" is used to mean introducing at least one of the compounds of the present invention to an organ, tissue or region of a subject such that at least one of the compounds of the present invention can access or come into proximity to AChE and/or BChE and exert a biological effect on the enzyme. As used herein, acetylcholinesterase, or AChE, includes active AChE, covalently inactivated AChE or aged AChE. Moreover, "inactive AChE" includes covalently inactivated AChE or aged AChE. As used herein, butyrylcholinesterase, or BChE, includes active BChE, covalently inactivated BChE or aged BChE. Moreover, "inactive BChE" includes covalently inactivated BChE or aged BChE.

Of course, "administration" can also include administering a combination of compounds. Thus, administration may be in the form of dosing an organism with a compound or combination of compounds, such that the organism's circulatory system will deliver a compound or combination of compounds to the target area, including but not limited to a cell or cells, synaptic junctions and circulation. Administration may also mean that a compound or combination of compounds is placed in direct contact with an organ, tissue, area, region, cell or group of cells, such as but not limited to direct injection of the combination of compounds.

In select embodiments, a combination of compounds can be administered, thus the individual compounds can also be said to be coadministered with one another. As used herein, "coadminister" indicates that each of at least two compounds is administered during a time frame wherein the respective periods of biological activity or effects overlap. Thus the term coadminister includes sequential as well as coextensive administration of the individual compounds, at least one of which is a compound of the present invention. Accordingly, "administering" a combination of compounds according to some of the methods of the present invention includes sequential as well as coextensive administration of the individual compounds of the present invention. Likewise, the phrase "combination of compounds" indicates that the individual compounds are coadministered, and the phrase "combination of compounds" does not mean that the compounds must necessarily be administered contemporaneously or coextensively. In addition, the routes of administration of the individual compounds need not be the same.

In select embodiments, at least one compound of the present invention is coadministered with an agent that will reactivate covalently inactivated AChE and/or inactivated BChE. Examples of agents that can reactivate covalently inactivated AChE, i.e., "rescue covalently inactivated AChE," or covalently inactivated BChE, i.e., "rescue covalently inactivated BChE," include but are not limited to oximes. Examples of oximes that can be coadministered with at least one compound of the invention include but are not limited to 2-pralidoxime ("2-PAM") and 1-(2'-hydroxyiminomethyl-1'-pyridinium)-3-(4'-carbamoyl-1-pyridinium) ("HI-6"). In specific embodiments of the present invention, at least one of the compounds of the present invention may be administered with, before or after an agent that will reactivate covalently inactivated AChE and/or BChE. The coadministration of these compounds may be as a treatment or as a prophylactic administration.

As used herein and unless otherwise indicated, the phrase "therapeutically effective amount" of a compound or combination of compounds of the invention is measured by the therapeutic effectiveness of a compound of the invention, wherein at least one adverse effect of deactivated AChE and/or BChE is ameliorated, alleviated reduced or prevented.

The terms "treat" and "treatment" may or may not refer to an amelioration of at least one discernible symptom associated with inactivation of AChE and/or BChE. The term "treat" can be used in the context of a subject that has been exposed to or is suspected of having been exposed to a compound known to inactivate AChE and/or BChE, such as but not limited to, an organophosphate, prior to the onset of any discernable or measurable symptom. For example, the term treat can mean administering at least one of the compounds of the present invention to a subject that was exposed to or suspected of being exposed to a nerve toxin, such as sarin, prior to the onset of any noticeable symptom of sarin poisoning. In another embodiment, "treatment" or "treat" refers to inhibiting or interfering with the aging of AChE and/or BChE after AChE and/or BChE has been covalently deactivated. Of course, the term "treat" can also be used in the context of a subject that is exhibiting one or more symptoms or signs of inactivated AChE and/or BChE. In yet another embodiment, "treatment" or "treat" refers to delaying the onset of a physical parameter or symptom of inactivated AChE and/or BChE.

When administration is for the purposes of "preventing" or interfering with the inactivation of AChE and/or BChE ("prophylactic administration"), the compound or combination of compounds is provided in advance of any visible or detectable symptom. The prophylactic administration of the compound or combination of compounds serves to attenuate subsequently arising symptoms or physical parameters or reduce the possibility of symptoms from arising altogether. Thus, as used herein, the term "prevent" as used in connection with administering the compound or combination of compounds of the present invention, is used to indicate the timing of the administration, i.e., before a detectable symptom arises, rather than indicate a complete removal of the possibility of developing any symptoms associated with inactivation of AChE and/or BChE. The term "prevent" can thus also mean that the compounds and methods of the present invention are intended to "reduce the likelihood" that a symptom of inactivated AChE and/or BChE will appear or become detectable.

The invention provides methods of treatment and prophylaxis by administration to a patient of a therapeutically effective amount of a compound or combination of compounds of the invention. The patient can be a mammal, including, but not limited to, an animal such as a cow, horse, sheep, pig, cat, dog, mouse, rat, rabbit, guinea pig, etc., and a human or non-human primate.

Each of the individual compounds that are administered in conjunction with the methods of the present invention can be administered orally. Each of the individual compounds of the invention may also be administered by any other convenient route, for example, by infusion or bolus injection, by absorption through epithelial or mucocutaneous linings (e.g., oral mucosa, rectal and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer at least one of the compounds of the invention. Methods of administration of the individual compounds include but are not limited to intradermal, intramuscular, intraperitoneal, intravenous, subcutaneous, intranasal, epidural, oral, sublingual, intranasal, intracerebral, intravaginal, transdermal, rectal, pulmonary or topical, particularly to the ears, nose, eyes, or skin. The preferred mode of administration is left to the discretion of the practitioner, and will depend, in part, upon the site of the medical condition. In most instances, administration will result in the release of one or more compounds of the invention into the bloodstream and subsequently into the central and/or peripheral nervous system.

In specific embodiments, it may be desirable to administer one or more compounds of the combination locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of the invention can be formulated as a suppository, with traditional binders and vehicles such as triglycerides.

In another embodiment, the compounds of the invention can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, at least one of the compounds used in the methods of the invention can be delivered in a controlled release system. In one embodiment, a pump may be used (see Langer, supra; Sefton, 1987, CRC Crit. Ref. Biomed. Eng. 14:201; Buchwald et al., 1980, Surgery 88:507 Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled-release system can be placed in proximity of an organ, e.g., the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, 1990, Science 249:1527-1533) may be used.

The present methods can also deliver a therapeutically effective amount of a compound or combination of compounds together with a suitable amount of a pharmaceutically acceptable vehicle so as to provide a form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. In one embodiment, when administered to a patient, the combination of compounds of the invention and pharmaceutically acceptable vehicles are sterile. Water and/or oils are one vehicle when the combination of compounds of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present combination of compounds, if desired, can also contain minor amounts of wetting or emulsifying agents, or pH buffering agents.

Each of the individual compounds to be administered can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in Remington's Science and Practice of Pharmacy (21st ed., Hendrickson, R., et al., Eds., Lippincott Williams & Wilkins, Baltimore, Md. (2006)), which is incorporated by reference.

Typically, when the individual compounds of the invention are administered intravenously, the compounds are in sterile isotonic aqueous buffered solutions. Where necessary, the individual compounds of the invention may also include a solubilizing agent. The individual compounds of the invention for intravenous administration may optionally include a local anesthetic such as lidocaine to ease pain at the site of the injection.

In one embodiment, individual compounds are supplied either together in a unit dosage form or separately. Regardless, compounds may be supplied, for example, as a dry lyophilized powder or water free concentrate in a hermetically sealed container such as an ampoule indicating the quantity of active agent. Where the compound or combination of compounds of the invention are to be administered by infusion, they can be dispensed, for example, with an infusion bottle containing sterile pharmaceutical grade water or saline. Where the compound or combination of compounds of the invention is administered by injection, an ampoule of sterile water for injection or saline can be provided so that the ingredients may be mixed prior to administration.

In one embodiment, the individual compounds can be administered orally. Compositions for oral delivery may be in the form of tablets, lozenges, aqueous or oily suspensions, granules, powders, emulsions, capsules, syrups, or elixirs, for example. Orally administered compositions may contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

The amount of each individual compounds to be administered will depend on the nature or severity of the symptoms or even the level of exposure to an agent that inactivates AChE, and can be determined by standard clinical techniques. In addition, in vitro or in vivo assays may optionally be employed to help identify optimal dosage ranges for each of the components of the combination. The precise dose of each component to be employed will also depend on the route of administration and the seriousness of the disease or disorder, and a practitioner can determine these doses based upon each patient's circumstances. In general, however, suitable dosage ranges for oral administration are generally about 0.001 milligram to 200 milligrams of a compound of the invention per kilogram body weight. In specific embodiments of the invention, the oral dose for each component is 0.01 milligram to 70 milligrams per kilogram body weight, more specifically 0.1 milligram to 50 milligrams per kilogram body weight, more specifically 0.5 milligram to 20 milligrams per kilogram body weight, and yet even more specifically 1 milligram to 10 milligrams per kilogram body weight. The dosage amounts described herein refer to individual amounts administered.

In general, suitable dosage ranges for intravenous (i.v.) administration of individual components are 0.01 milligram to 100 milligrams per kilogram body weight, 0.1 milligram to 35 milligrams per kilogram body weight, and 1 milligram to 10 milligrams per kilogram body weight. In general, suitable dosage ranges for intranasal administration of the individual components are generally from about 0.01 pg/kg body weight to 1 mg/kg body weight. In general, suppositories generally contain between about 0.01 milligram to 50 milligrams of a compound per kilogram body weight and may comprise active ingredient in the range of 0.5% to 10% by weight. Effective doses may be extrapolated from dose-response curves derived from in vitro or animal model test systems. Such animal models and systems are well known in the art.

The invention also provides pharmaceutical packs or kits comprising one or more containers filled with one or more compounds to be administered in practicing the methods of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a certain embodiment, the kit contains more than one compound.

The examples herein are for illustrative purposes only and they are not intended to limit the scope of the invention in any way.

EXAMPLES

Synthesis of Compound 101

Synthesis of compound 101 is shown in Scheme 1, below, and can be carried out starting with commercially available precursors A and B. Compound A is 3,5-diamino-4-chlorotoluene (IUPAC name: 2-chloro-5-methylbenzene-1,3-diamine) of molecular formula $C_7H_9ClN_2$. This compound is available from AKos. The amino groups of compound A are protected with such groups as Boc, Ts, Cbz or other suitable amino protective groups, wherein Boc is tert-butyloxycarbonyl; Ts is a tosyl group such as p-toluenesulfonyl; and Cbz is carboxybenzyl. The reaction for adding the protection groups to amines is standard.

Compound B is an N-protected α-amino epoxide, specifically N-Boc-2,3-epoxypropylamine. This compound is commercially available from Sigma-Aldrich, but can also be produced according to synthesis described in Org. Process Res. Dev., 2011, 15 (2), pp 331-338, which is incorporated by reference. N-protected compound A and B can be coupled using Ni-catalyzed reaction described in J. Am. Chem. Soc., 2014, 136 (1), pp 48-51, which is incorporated by reference, with ring opening of the epoxide of compound B. The groups protecting the amines in compounds A and B are removed after coupling is completed using standard techniques. In instances where the reactivity of the chloride in the N-protected compound A may not be sufficient, the chloride may be substituted for more reactive Br or I, following the procedure described in Synlett 2003(8): pp 1145-1148, which is incorporated by reference.

Scheme 1a - Protect Compound A's amino groups with Ts compound

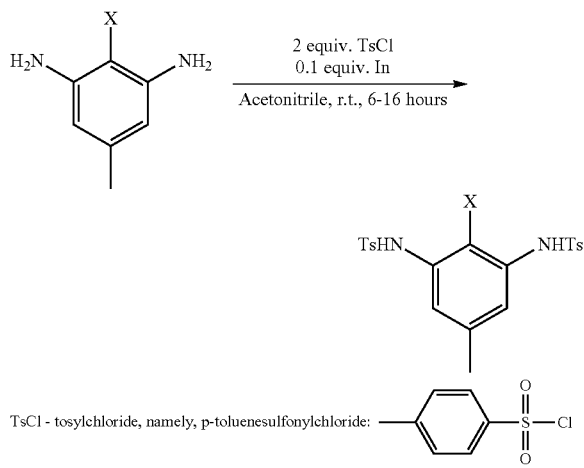

TsCl - tosylchloride, namely, p-toluenesulfonylchloride:

X - Cl, Br, or I

Scheme 1b - Main Reaction Step

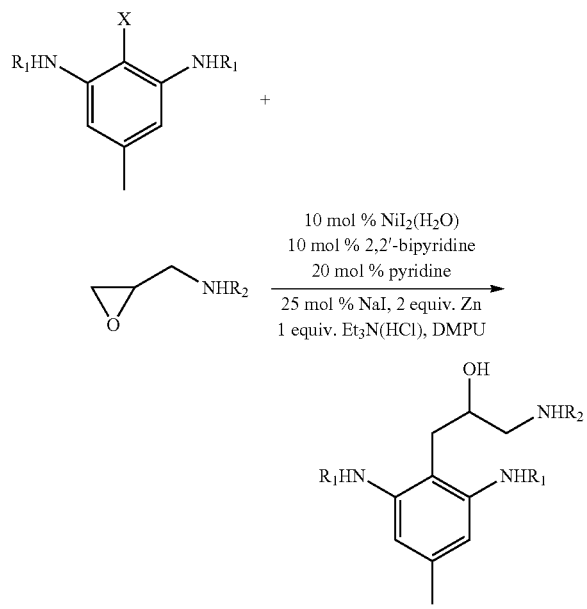

DMPU - 1,3-dimethyl-3,4,5,6-tetrahydro-2-pyrimidinone
Et - ethyl
$R_1$ - Boc, Ts, or Cbz
$R_2$ - Boc
Boc - tert-butyloxycarbonyl
Ts - tosyl, namely, p-toluenesulfonyl
Cbz - carboxybenzyl
X - Cl, Br, or I

Scheme 1c - Deprotect Ts-protected amino groups of the final product

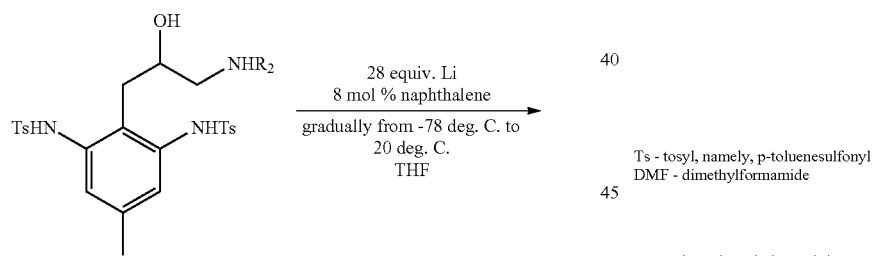

THF - tetrahydrofuran
$R_2$ - Boc
Boc - tert-butyloxycarbonyl
Ts - tosyl, namely, p-toluenesulfonyl

Scheme 1d - Deprotect Boc-protected amino groups of the final product following Ts-deprotection

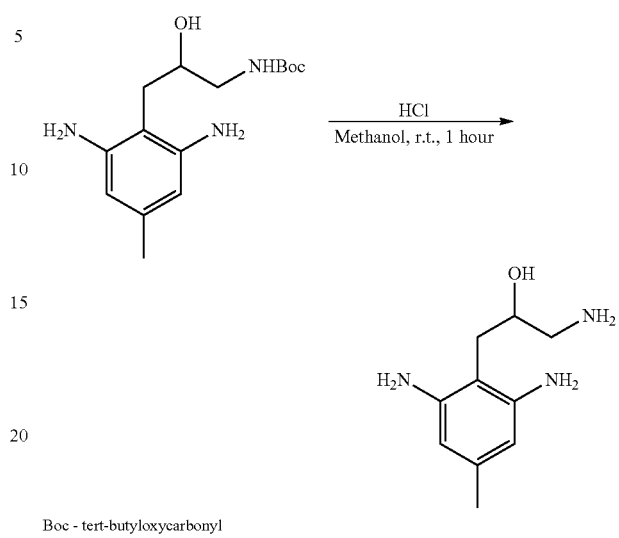

Boc - tert-butyloxycarbonyl

Scheme 1e - Optional conversion of Cl compound to Br derivative

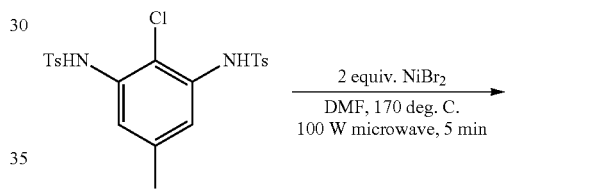

Ts - tosyl, namely, p-toluenesulfonyl
DMF - dimethylformamide

What is claimed is:
1. A compound of Formula I:

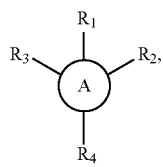

I or a pharmaceutically acceptable salt thereof,
wherein

is a 5- or 6-membered substituted or unsubstituted aromatic ring or a 5- or 6-membered substituted or unsubstituted cycloalkyl;

$R_1$ is $R_5$—C($R_6$)(OH)—$R_7$—C($R_8$)(NH$_2$)—$R_9$;

$R_2$ is NH$_2$;

$R_3$ is NH$_2$; wherein $R_3$ is ortho to $R_1$ and $R_1$ is ortho to $R_2$;

$R_4$ is selected from the group consisting of H, CN, OR$_{10}$, S(O)$_{0-2}$R$_{10}$, C$_{1-6}$ alkyl, C$_{1-6}$ alkene, NR$_{11}$R$_{12}$ and C(O)NR$_{13}$R$_{14}$;

$R_5$ is selected from the group consisting of a bond, C$_{1-4}$ alkylene and C$_{1-4}$ alkenylene;

$R_6$ is selected from the group consisting of H and C$_{1-3}$ alkyl;

$R_7$ is selected from the group consisting of a bond, substituted or unsubstituted C$_{1-3}$ alkylene and substituted or unsubstituted C$_{1-3}$ alkenylene;

$R_8$ is selected from the group consisting of H, C(O)NHR$_{15}$ and C(O)OR$_{15}$;

$R_9$ is selected from the group consisting of H, CN, —C(R$_6$)$_2$OH, OR$_8$, NR$_{11}$R$_{12}$, C(O)NR$_{11}$R$_{12}$, C$_{1-6}$ alkyl and C$_{1-6}$ alkene;

$R_{10}$ is selected from the group consisting of H, C$_{1-3}$ alkyl and C$_{6-12}$ aryl;

$R_{11}$, $R_{12}$, $R_{13}$, and $R_{14}$ are independently selected from the group consisting of H, C$_{1-4}$ alkyl and C$_{1-4}$ alkene, wherein at least one of $R_{11}$ and $R_{12}$ is H; and $R_{15}$ is selected from the group consisting of H and C$_{1-3}$ alkyl.

2. A compound selected from:

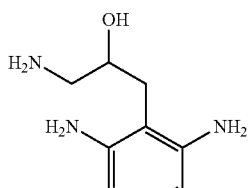
101

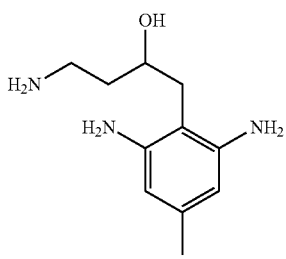
102

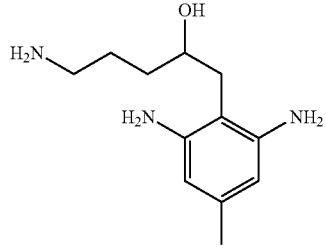
103

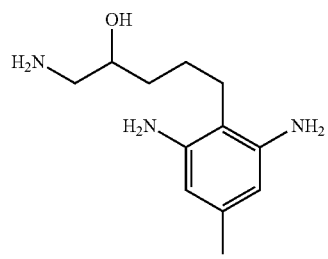
104

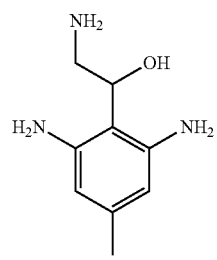
105

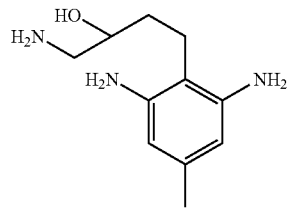
106

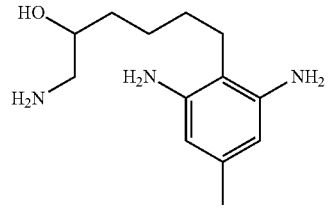
107

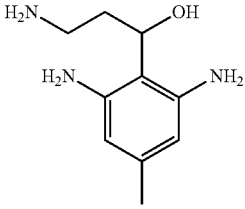
108

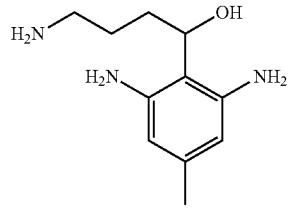
109

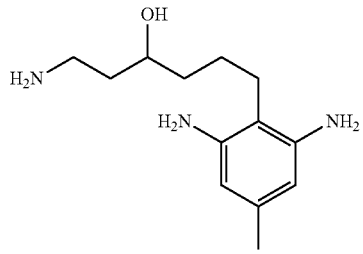
110

111
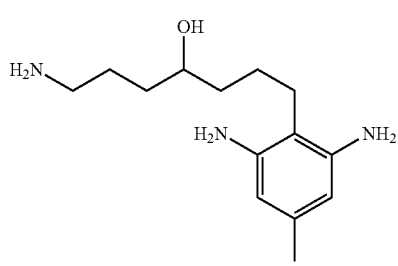
112
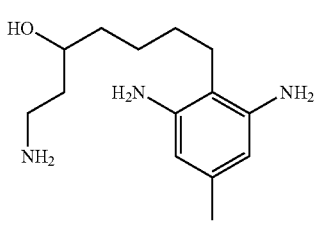
113
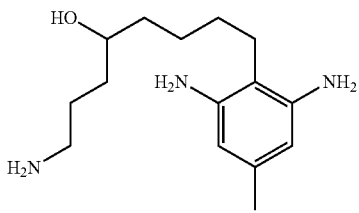
114
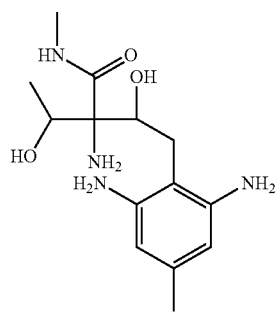
115
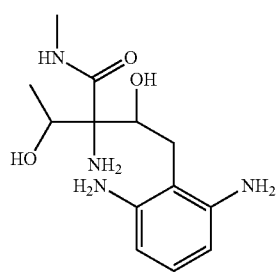
116
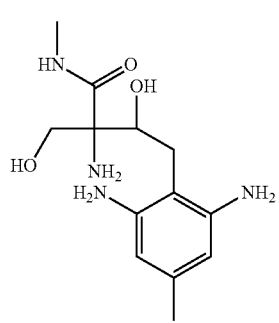
117
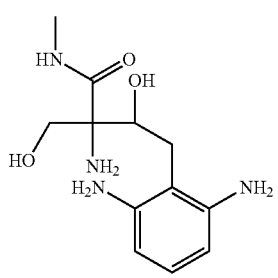
118
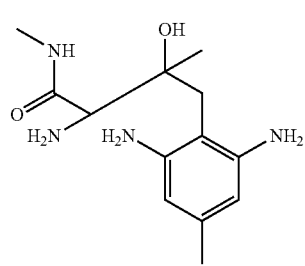
119
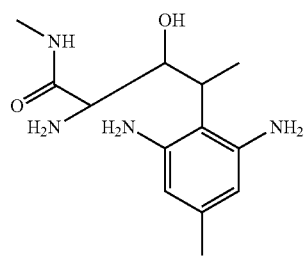
120
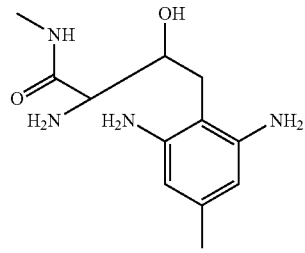
201
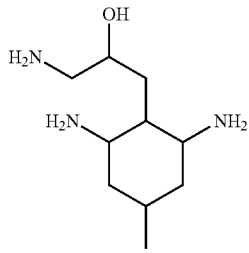
202
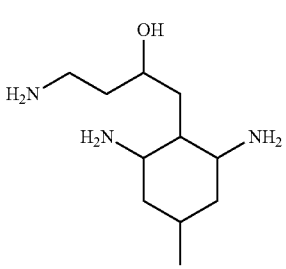

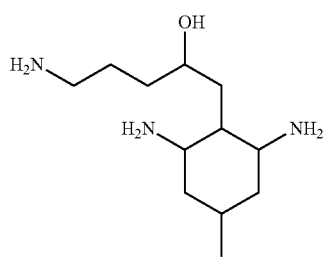
203
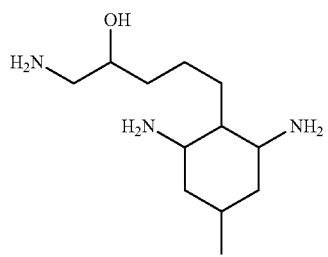
204
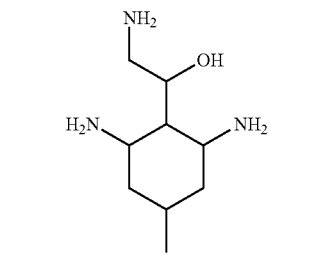
205
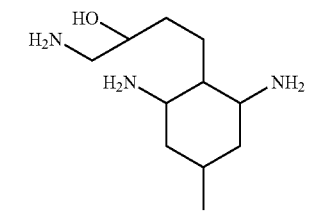
206
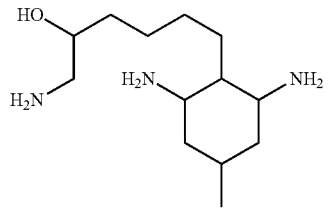
207
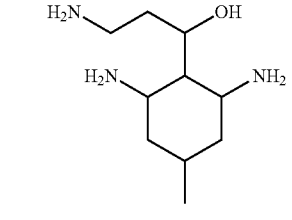
208
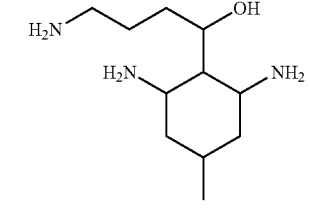
209
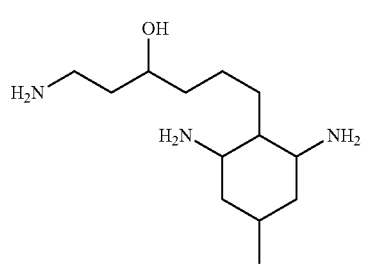
210
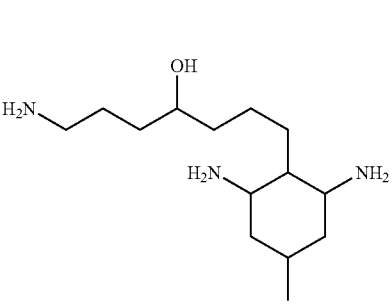
211
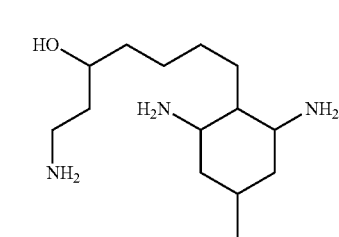
212
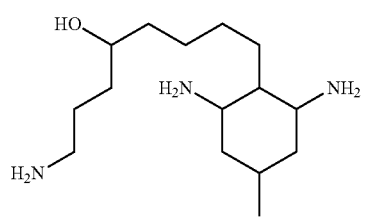
213
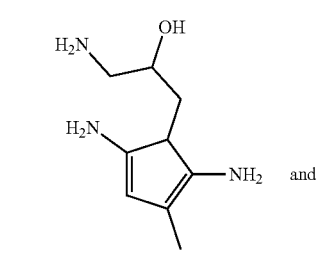
401
and
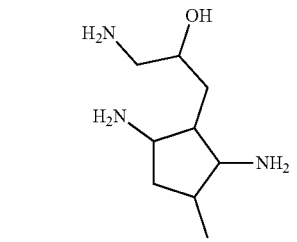
501
or a pharmaceutically acceptable salt thereof.

3. The compound of claim 2, wherein the compound is

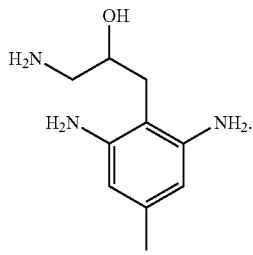

4. A method of reactivating an inactivated acetylcholinesterase (AChE) or preventing inactivation of an AChE in a subject in need thereof, the method comprising administering to the subject a therapeutically effective amount of a compound of Formula I of claim 1, or a pharmaceutically acceptable salt thereof.

5. A method of reactivating an inactivated acetylcholinesterase (AChE) or preventing inactivation of an AChE in a subject in need thereof, the method comprising administering to the subject a therapeutically effective amount of a compound of claim 2, or a pharmaceutically acceptable salt thereof.

6. The method of claim 5, wherein the compound is

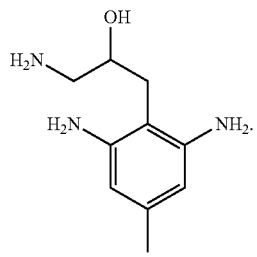

7. The method of claim 4, wherein the method is directed to reactivating an inactivated AChE and the inactivated AChE is an aged AChE.

8. The method of claim 4, wherein the method is directed to preventing inactivation of an AChE and the subject was exposed to an inactivating agent.

9. The method of claim 8, wherein the compound of Formula I is co-administered with an oxime.

10. The method of claim 8, wherein the subject was exposed to sarin, soman or cyclosarin prior to administration of the compound of Formula I.

11. The method of claim 5, wherein the method is directed to reactivating an inactivated AChE and the inactivated AChE is an aged AChE.

12. The method of claim 5, wherein the method is directed to preventing inactivation of an AChE and the subject was exposed to an inactivating agent.

13. The method of claim 12, wherein the compound is co-administered with an oxime.

14. The method of claim 12, wherein the subject was exposed to sarin, soman or cyclosarin prior to administration of the compound.

* * * * *